US011107703B2

(12) United States Patent
Tolosa et al.

(10) Patent No.: US 11,107,703 B2
(45) Date of Patent: Aug. 31, 2021

(54) MONOLITHIC, BIOCOMPATIBLE FEEDTHROUGH FOR HERMETICALLY SEALED ELECTRONICS AND METHODS OF MANUFACTURE

(71) Applicant: Neuralink Corp., Fremont, CA (US)

(72) Inventors: Vanessa M. Tolosa, Emeryville, CA (US); Camilo A. Diaz-Botia, Monte Sereno, CA (US); Supin Chen, San Ramon, CA (US); Felix Deku, Alameda, CA (US); Yu Niu Huang, Alameda, CA (US); Mark J. Hettick, San Leandro, CA (US); Zachary M. Tedoff, Oakland, CA (US)

(73) Assignee: Neuralink Corp., Fremont, CA (US)

( * ) Notice: Subject to any disclaimer, the term of this patent is extended or adjusted under 35 U.S.C. 154(b) by 0 days.

(21) Appl. No.: 16/924,442

(22) Filed: Jul. 9, 2020

(65) Prior Publication Data
US 2021/0013051 A1 Jan. 14, 2021

Related U.S. Application Data

(60) Provisional application No. 62/873,751, filed on Jul. 12, 2019.

(51) Int. Cl.
*H01L 21/50* (2006.01)
*A61N 1/05* (2006.01)
(Continued)

(52) U.S. Cl.
CPC ............ *H01L 21/50* (2013.01); *A61N 1/0531* (2013.01); *B81C 1/00095* (2013.01);
(Continued)

(58) Field of Classification Search
CPC . H01L 21/50; H01L 24/14; H01L 2021/6027; H01L 23/043; H01L 23/00;
(Continued)

(56) References Cited

U.S. PATENT DOCUMENTS 6,592,519 B1 * 7/2003 Martinez ................ A61B 5/145
600/309
8,285,394 B1 * 10/2012 Wessendorf ....... A61N 1/36046
607/116
(Continued)

OTHER PUBLICATIONS

Application No. PCT/US2020/041377, International Search Report and Written Opinion, dated Oct. 8, 2020, 7 pages.
(Continued)

*Primary Examiner* — Alexander O Williams
(74) *Attorney, Agent, or Firm* — Kilpatrick Townsend & Stockton LLP

(57) ABSTRACT

Methods of manufacturing a biocompatible, hermetic feedthrough monolithically integrated with a biocompatible ribbon cable are described, as well as the resulting devices themselves. The hermetic feedthrough is created by placing glass over a mold of doped silicon or other material with a higher melting temperature than the glass and heating it to reflow the glass into the mold. The glass is then ground or otherwise removed to reveal a flat surface, and tiny pillars that were in the mold are isolated in the glass to form electrically conductive vias. The flat surface is used to cast a polymer and build up a ribbon cable, photolithographically or otherwise, that is monolithically attached to the vias.

23 Claims, 8 Drawing Sheets

(51) Int. Cl.
*H01B 7/08* (2006.01)
*H01L 23/043* (2006.01)
*H01L 23/00* (2006.01)
*C03C 19/00* (2006.01)
*B81C 1/00* (2006.01)
*H01L 21/60* (2006.01)

(52) U.S. Cl.
CPC ............... *C03C 19/00* (2013.01); *H01B 7/08* (2013.01); *H01L 23/043* (2013.01); *H01L 24/14* (2013.01); *B81B 2201/036* (2013.01); *H01L 2021/6027* (2013.01)

(58) Field of Classification Search
CPC .......... H01B 7/08; A61N 1/0531; A61N 1/05; C03C 19/00; B81C 1/00095; B81C 2201/036; B81C 1/00; B81B 2201/036
USPC ........................................................ 257/687
See application file for complete search history.

(56) References Cited

U.S. PATENT DOCUMENTS

| 8,707,734 | B2 | 4/2014 | Haque et al. | |
|---|---|---|---|---|
| 10,272,253 | B2* | 4/2019 | Seitz | H01B 17/303 |
| 10,463,285 | B2* | 11/2019 | Boone | A61B 5/02433 |
| 2006/0173259 | A1* | 8/2006 | Flaherty | A61B 5/685 |
| | | | | 600/331 |
| 2008/0314865 | A1 | 12/2008 | Ok et al. | |
| 2011/0091687 | A1 | 4/2011 | Haque et al. | |
| 2012/0217648 | A1 | 8/2012 | Park et al. | |
| 2013/0184796 | A1 | 7/2013 | Marzano et al. | |
| 2015/0069618 | A1 | 3/2015 | Gudeman et al. | |
| 2016/0029956 | A1* | 2/2016 | Rowland | A61B 5/076 |
| | | | | 600/302 |
| 2016/0045724 | A1* | 2/2016 | Lee | B23K 26/40 |
| | | | | 604/20 |
| 2018/0178016 | A1* | 6/2018 | Frustaci | H01G 4/35 |
| 2018/0197661 | A1* | 7/2018 | Seitz | A61N 1/3754 |
| 2020/0085375 | A1 | 3/2020 | Tolosa et al. | |
| 2020/0086111 | A1 | 3/2020 | Young et al. | |
| 2020/0215335 | A1* | 7/2020 | McLaughlin | A61N 1/0553 |
| 2020/0222010 | A1* | 7/2020 | Howard | A61B 5/4836 |
| 2020/0315477 | A1* | 10/2020 | Constandinou | A61N 1/37229 |
| 2021/0007602 | A1* | 1/2021 | Seo | A61B 5/0017 |

OTHER PUBLICATIONS

Chung et al., A Polymer Probe-Based System for High Density, Long-Lasting Electrophysiological Recordings Across Distributed Neuronal Circuits, http://dx.doi.org/10.1101/242693, Jan. 4, 2018.

P. Merz et al., A Novel Micromachining Technology for Structuring Borosilicate Glass Substrates, Transducers '03, pp. 258-261, Fraunhofer Institute for Silicon Technology (FHG ISIT), Itzehoe, Germany.

A. Tooker et al., "Towards a Large-Scale Recording System: Demonstration of Polymer-Based Penetrating Array for Chronic Neural Recording," 36th Annual International Conference of the IEEE Engineering in Medicine and Biology Society, Aug. 2014, LLNL-CONF-655518, Chicago, IL.

\* cited by examiner

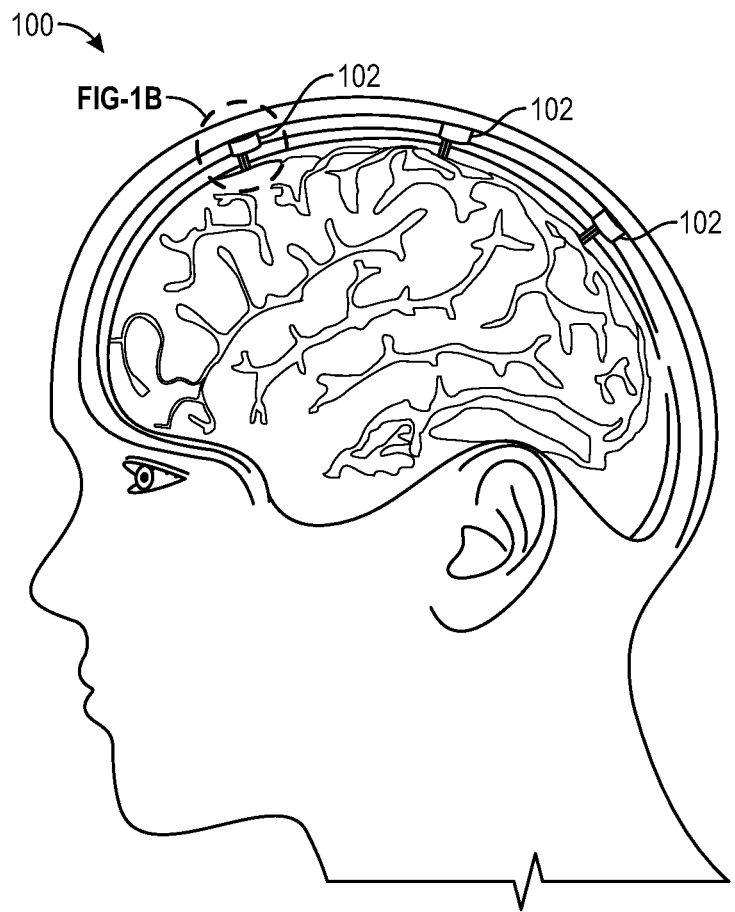
FIG. 1A
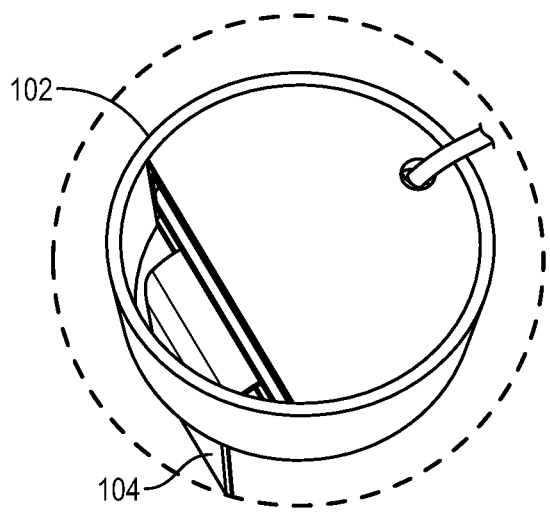 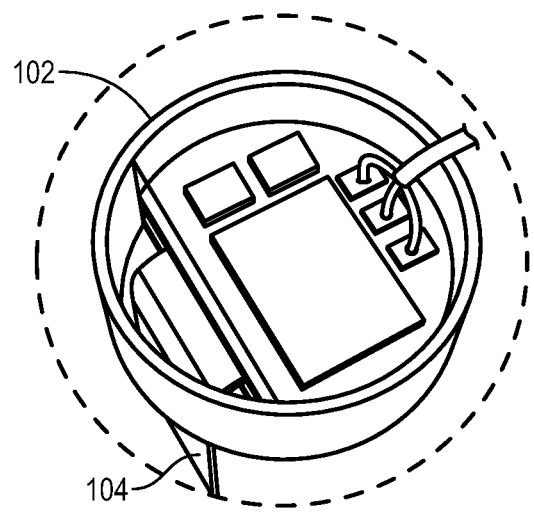
FIG. 1B   FIG. 1C

MONOLITHIC, BIOCOMPATIBLE FEEDTHROUGH FOR HERMETICALLY SEALED ELECTRONICS AND METHODS OF MANUFACTURE

CROSS-REFERENCES TO RELATED APPLICATIONS

This application claims the benefit of U.S. Provisional Patent Application No. 62/873,751, filed Jul. 12, 2019, which is hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Invention

Embodiments of the present invention generally relate to solid state devices connecting through a glass-based hermetic seal to thin-film circuits for biological applications. More specifically, embodiments relate to apparatuses and processes for manufacturing printed or thin film circuits with electrical connections through silicon vias in a glass substrate to other circuitry.

2. Description of the Related Art

Electronic devices implanted within animals and humans often require a hermetically sealed housing. The housing keeps body fluids from corroding and degrading silicon-based or metallic electrical components inside. It also keeps materials that are not biocompatible from leaching into body tissue. This can be especially important for the electrolytes of batteries.

To transmit or receive voltage, current, or other signals beyond the housing, the components often must be connected with wires whose conductive paths go through the housing. The area where the conductive path passes through the housing is often called a "hermetic feedthrough" or "hermetic substrate."

Hermetic feedthroughs often consist of a flat panel that has been drilled through by a computer numerical control (CNC) machine drill bit, water drilling, or by laser drilling. Each of these introduces stresses in the material, potentially causing microcracks. For example, machine drilling tears away bits of metal, and laser drilling intensely heats the material causing some to vaporize.

The holes are later filled with conductive material to form "vias." The more holes that there are to be formed, the longer it takes to drill the feedthrough. And the more holes there are, the more opportunities there are for leaks.

Ocular implants and brain-machine interfaces (BMIs) benefit from many separate, direct connections with their organs. Hundreds, and even thousands, of connections are preferable so that as many photoreceptors or neurons as possible can be stimulated or sampled. Hermetic feedthroughs having hundreds or thousands of vias are prohibitively expensive to produce by drilling, both in terms of time, tooling, and yield. Each hole must be filled with conductive material to form a via, which adds to the expense. And then there may be a leak or other defect in one or more of the hundreds or thousands of vias that is next to impossible to pinpoint.

Additionally, flexible arrays that connect with conventional feedthroughs sometimes employ ball seal connectors. Ball seal connectors are quite large. Not using ball seal connectors often results in connections that are not quite hermetically sealed. Because of these and other reasons, vias in hermetic feedthroughs with a pitch less than 400 μm using biocompatible materials is elusive.

There is a need in the art for better electrical interconnections through hermetically sealed feedthroughs for surgically implanted medical devices, and processes for manufacturing them.

BRIEF SUMMARY

Generally, a hermetic feedthrough is fashioned by photolithographically forming a mold out of silicon with tiny doped pillars where vias should go, melting glass around the pillars and letting it cool, grinding it flat or otherwise planarizing on both sides to leave a glass panel with doped silicon vias, and then microfabricating a thin film ribbon cable on one side of the flat glass. Conductors within the ribbon cable are electrically attached to the vias. Metal pads can be fashioned over the vias, and an insulating layer deposited as well. The other side of the glass panel is also ground flat so that IC chips and other electronics may be connected to the vias. Spacers and/or lids may be sealed to its surfaces to form a hermetically sealed electrical device.

Some embodiments of the present invention are related to a method of manufacturing a biocompatible hermetic feedthrough with an integrated ribbon cable. The method includes placing a glass composition over and/or between pillars of doped silicon, heating the glass composition to a reflow temperature such that at least a portion of the heated glass composition flows around the pillars, allowing the glass composition to solidify and encase the pillars in solidified glass, grinding or otherwise planarizing a top of the solidified glass sufficient to expose tops of the encased pillars, depositing a biocompatible insulative layer over the solidified glass, casting an uncured polymer over the biocompatible insulative layer and allowing the polymer to cure into a flat polymer sheet, patterning conductive traces on the polymer sheet to connect with the encased pillars, coating the conductive traces with polymer to form a ribbon cable, and planarizing a bottom of the solidified glass sufficient to expose bottoms of the encased pillars, thereby electrically isolating the pillars from each other and forming conductive vias through a hermetic feedthrough of solidified glass.

The biocompatible insulative layer covering the solidified glass composition can include silicon carbide or $Al_2O_3$+ $HfO_2/ZrO_2$, among other insulators.

The method can include etching a substrate of doped silicon to create the pillars out of doped silicon. It can include replacing the pillars of silicon with pillars of metal by chemically etching away the silicon pillars and electroplating or additively filling metal in their place.

The method can include depositing metal caps over the tops of the encased pillars, wherein the conductive traces connect with the conductive vias through the metal caps. At least one of the metal caps on the bottom of the solidified glass can be elongated and overhang away from a respective via.

The method can include depositing a second biocompatible insulative layer over the bottom of the solidified glass, and attaching an integrated circuit (IC) chip to the conductive vias on the bottom of the solidified glass. Attaching can include compressing a bump connection between the IC chip and at least one of the conductive vias. Attaching can include soldering, using anisotropic conductive film (ACF) connections, or applying epoxy. The method can include attaching a hermetically sealed walled housing around the IC chip and encasing the IC chip. Encasing the IC chip can include attaching a second hermetic interconnect to walls around the IC chip.

Planarizing can include grinding, polishing, lapping, fly cutting, laser ablating, or coating with a planarizing layer and etching. The planarizing of the bottom of the solidified glass can occur before casting the uncured polymer.

Some embodiments include a monolithic, biocompatible feedthrough apparatus including a glass substrate having doped silicon conductive vias, a biocompatible insulative layer covering a surface of the glass substrate, a polymer ribbon cable formed from uncured polymer curing on the biocompatible insulative layer, and conductive traces within the polymer ribbon cable and connecting with the conductive vias.

The biocompatible insulative layer covering the surface of the glass substrate can include silicon carbide or $Al_2O_3$+ $HfO_2/ZrO_2$. among other insulators.

The apparatus can further include biocompatible metal caps covering ends of the conductive vias, wherein the conductive traces connect with the conductive vias through the metal caps. At least one of the metal caps can be elongated and overhang away from a respective via.

The apparatus can include a second biocompatible insulative layer over a bottom of the glass substrate, and an integrated circuit (IC) chip attached to the conductive vias on the bottom of the glass substrate. The IC can be attached by compressing a bump connection between the IC chip and at least one of the conductive vias. The apparatus can include a hermetically sealed walled housing around the IC chip and encasing the IC chip.

BRIEF DESCRIPTION OF THE DRAWINGS

FIG. 1A is an illustrative side view of a human head with brain-machine interface (BMI) implants with hermetically sealed feedthroughs in accordance with an embodiment.

FIG. 1B is a perspective top view of an implant of FIG. 1A.

FIG. 1C is a perspective top view of the implant of FIG. 1B with its cover removed.

DETAILED DESCRIPTION

Hundreds or thousands of individual electrical connections can be made between electrodes on a microfabricated polymer-based ribbon cable in a subject's body and a hermetically sealed integrated circuit (IC) using a feedthrough described herein. The thousands of vias in the hermetic feedthrough are well sealed with minimal opportunities for leaks.

U.S. Pat. No. 8,707,734 to Haque et al., herein incorporated by reference, describes a method for embedding electrically conductive materials within glass by reflowing glass around features in a silicon mold. The electrically conductive materials can include a doped silicon composition. Such techniques can be used in the first part of some manufacturing embodiments in order to prepare a hermetic feedthrough.

FIG. 1A illustrates a human head with system 100 of three brain-machine interface (BMI) implants 102 set within holes in the subject's cranium (skull bone). They are located in different lobes, or areas of the brain, to capture or stimulate targeted sections. The holes, called "burr holes," are about 8 millimeters in diameter and drilled using specialized surgical tools. During surgery, thin film electrodes, sometimes numbering in the hundreds or thousands, are delicately inserted into the cortex at precise locations to avoid vasculature. The thin film electrodes merge into ribbon cable 104 at one end, which in turn is preconnected to the implant. Each implant is carefully set on top of the ribbon cable to cover the burr hole.

FIGS. 1B-1C show an implant with a ribbon cable extending below it. FIG. 1C shows the implant without its top cover. Within each implant is circuitry, including integrated circuit (IC) chips, capacitors, and other components. The ICs receive from, and/or transmit to, the thin film electrodes that are surgically implanted within the subject's cranium. The ICs can include analog-to-digital converters (ADC) and/or digital-to-analog converters (DAC) in order to convert analog signals in the brain to or from digital signals of a computer.

Sitting in the burr hole, the bottom of each implant, and the entire implant, are awash with cerebrospinal fluid (CSF) and other body fluids. These fluids are corrosive to the silicon in the IC chips as well as other circuit components and must be sealed away from them. Therefore, the components are isolated within the implant in a mostly-glass container that is biologically neutral. The components are carefully positioned to interface with the thin film ribbon cable of what may be thousands of individual electrodes.

Figure 2:
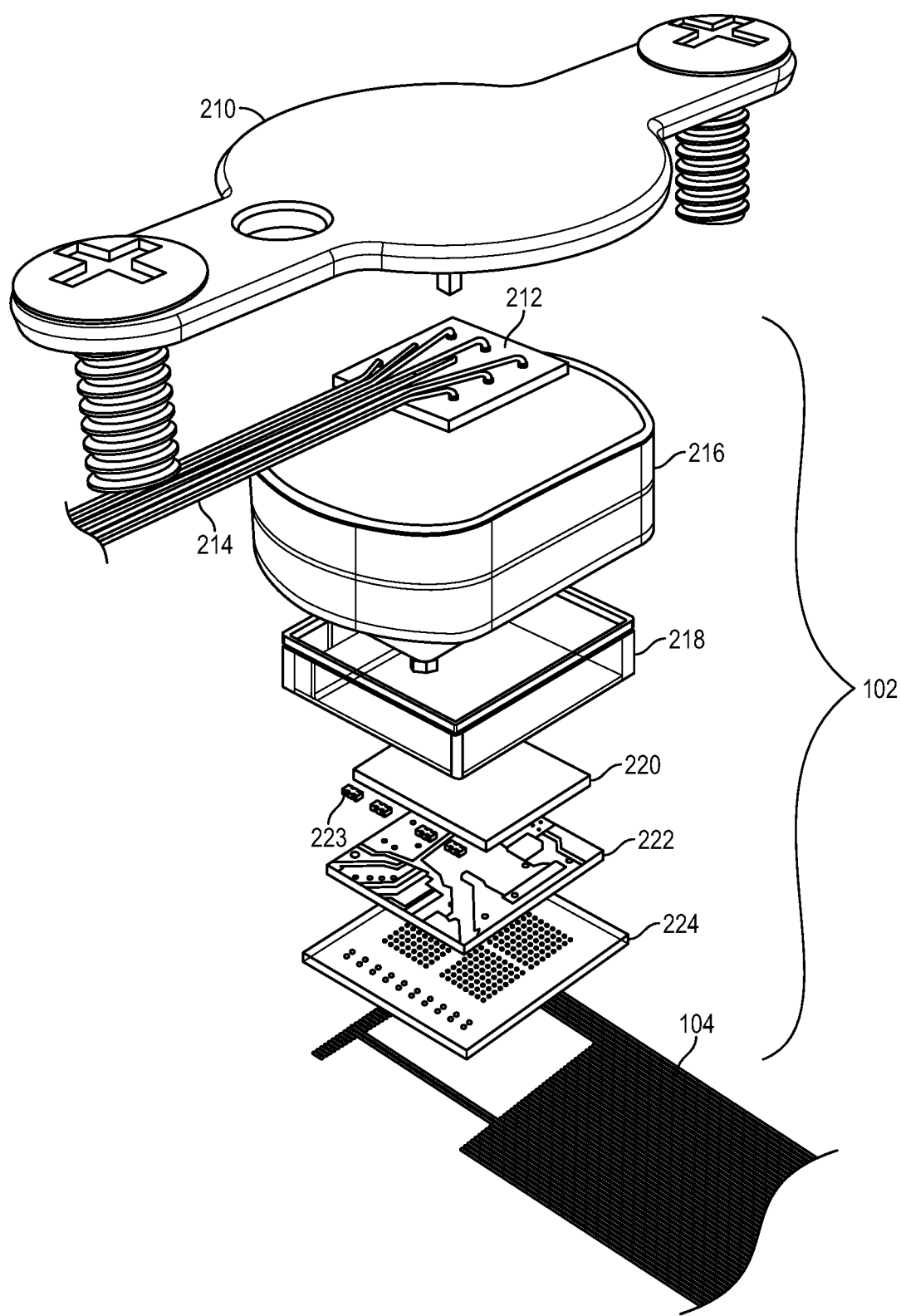
FIG. 2 is an exploded view of an implant of FIG. 1A along with a burr hole cover.

FIG. 2 is an exploded view of implant 102 and shows additional elements, such as burr hole cover 210 and additional packaging. The total height of the assembly fits within the average skull thickness of humans, which is about 6.5 mm for males and about 7.1 mm for females. After the assembly is surgically implanted in a burr hole, burr hole cover 210 is screwed to the cranium.

At the top of implant 102, just under burr hole cover 210, is cable 214. The cable may run to a different implant or off-body with several digital lines, or it may terminate in an antenna for wireless communication. In either case, cable 214 sends output from analog-to-digital converters (ADC)s in the IC chip below to other systems or bring input from those same systems to the chip for commands, processing, or stimulation. Cable 214 connects to hermetic seal 212.

Hermetic seal 212 electrically connects the cable through outer glass housing 216. Glass housing 216 protects hermetically sealed walled housing 218. It is this inner walled housing that encases the IC chip.

Hermetically sealed walled housing 218 covers IC chip 220, capacitors 223, and PC board 222. In the exemplary embodiment, housing 218 is approximately 5 millimeters (mm) in width and breadth and about 2-3 mm in height. Housing 218 is laser sealed against hermetic feedthrough 224, encasing the IC chip and other components. The empty volume inside hermetically sealed walled housing 218 that is not occupied by components may be encapsulated in an epoxy & silicone overmold.

Hermetic feedthrough 224 electrically connects components within housing 218 to a thin film flexible cable, otherwise called ribbon cable 104. This flex cable can have hundreds to thousands of conductive traces within it leading to individual electrodes. Built up directly on the glass of the hermetic feedthrough, it can be referred to as "monolithically formed" with the hermetic feedthrough. In the figure, ribbon cable 104 projects laterally from the bottom of the assembly. However, it turns downward when implanted, as shown in FIG. 1C.

The bottom two layers, hermetic feedthrough 224 and ribbon cable 104, involve manufacturing processes that are of particular interest and detailed below.

Figure 3:
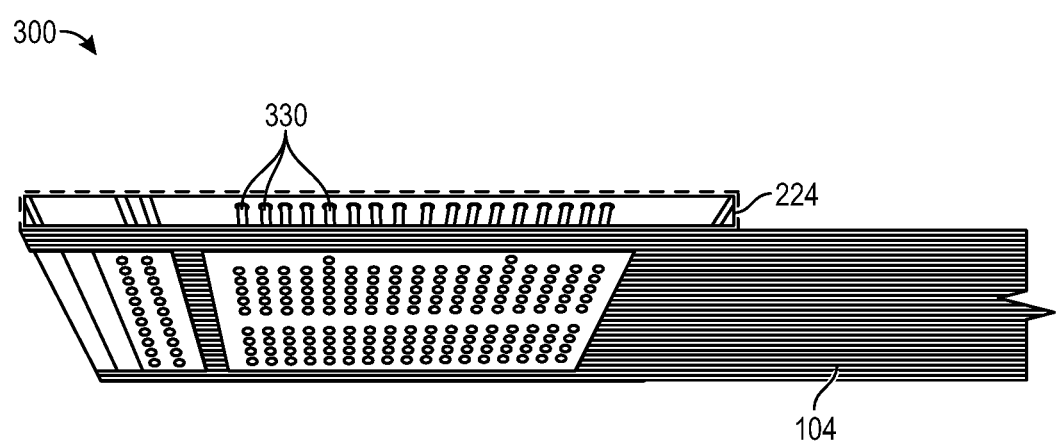
FIG. 3 is a perspective bottom view of a ribbon cable on the hermetically sealed feedthrough in of FIG. 1A.

FIG. 3 is a perspective bottom view of assembly 300 with ribbon cable 104 and its interconnects with hermetic feedthrough 224. Several layers of conductors within the ribbon cable keep the individual electrical signals apart. Individual vias within the cable connect the conductors to metal pads, or caps, on conductive vias 330 of hermetic feedthrough 224. Conductive vias 330, made of doped silicon, can be seen through the mostly transparent polymer. The polymer protects the conductors inside it from corrosion.

Forming hundreds or thousands of hermetically sealed conductive vias through glass is technically challenging. Just one crack, unfilled hole, or other flaw may result in a leak. A living brain moves considerably within its cranium quite frequently, so there may be tugging at the ribbon cable and conductive vias. The components inside are cramped without much room for sealant.

Figure 4:
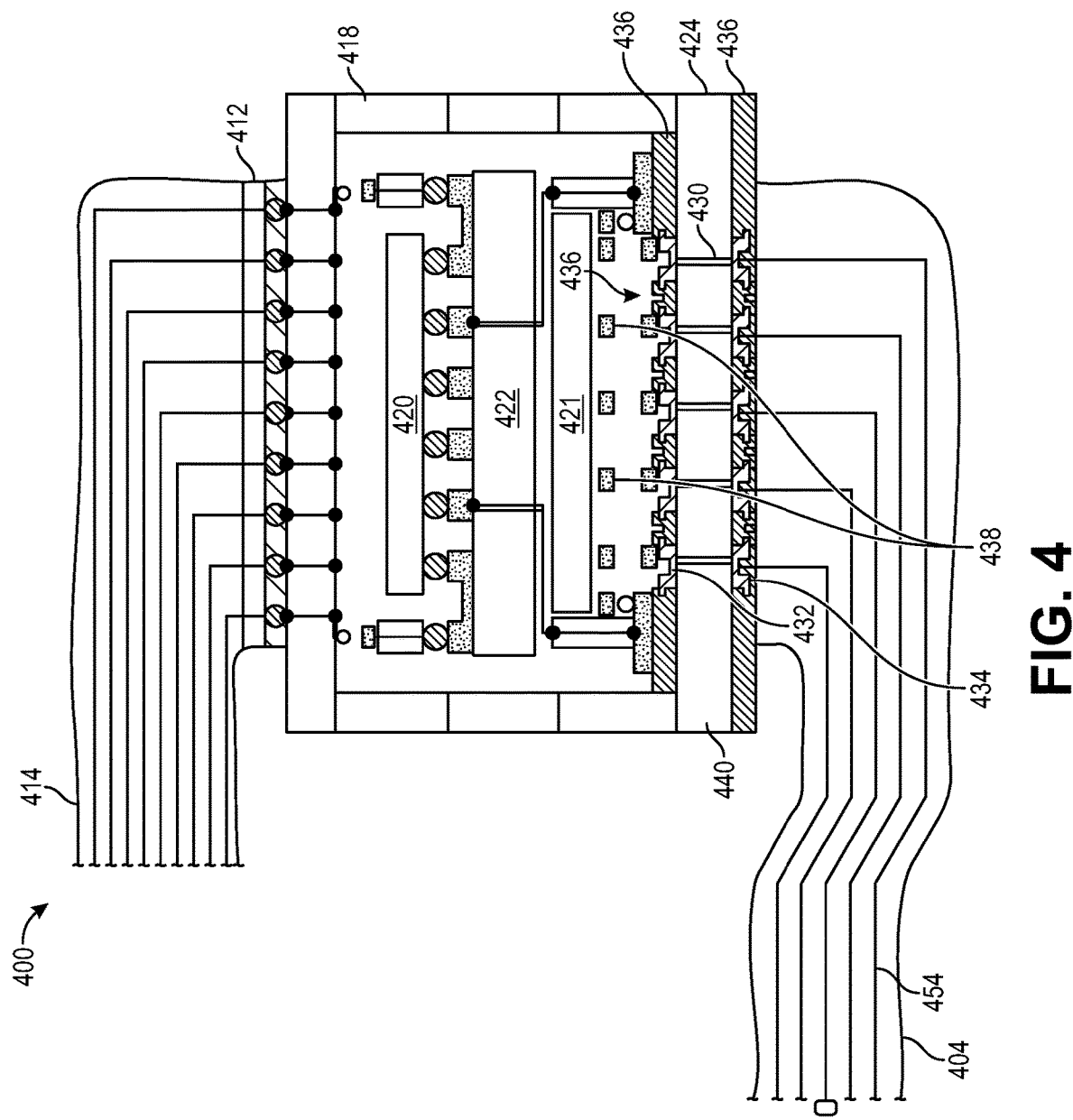
FIG. 4 is an elevation cross-section view schematic of a hermetically sealed chip in accordance with an embodiment.

FIG. 4 is an elevation cross-section view of sealed chip assembly 400. At the top of the exemplary assembly is cable 414 with a connector region passing to top feedthrough 412 on the top of hermetically sealed walled housing 418. The housing may have multiple walls stacked on top of each other. Each conductor from cable 414 passing through top feedthrough 412 is connected through a solder ball to conductive traces in the feedthrough. Between the connector and feedthrough is placed an epoxy underfill. An overmold is spread over the top of the connector for better sealing against body fluids. Underneath are active electronics.

Gold stud bumps connect to posts adjacent application specific integrated circuit (ASIC) 420 and to a ball grid array on the underside of the ASIC through a set of conductors and solder balls or alternative electrical connection. ASIC 420 may communicate with a lower ASIC 421 through other connections that route around lower ASIC 421 and get fed into lower ASIC 421 through a titanium, platinum, or gold connection.

A conductive pattern leads the traces to hermetic feedthrough 424. Hermetic feedthrough 224 includes glass substrate 440 and conductive, doped silicon vias 430. In the exemplary embodiment, hermetic feedthrough 424 is 300 µm thick. Other thicknesses are contemplated, such as, but not limited to, 200 to 600 µm.

Optional metal caps 432 and 434 are above and below conductive vias 430, respectively. The use of metal caps can help ensure that connections are secure and robust.

The metal caps may be elongated in one direction and overhang away from its underlying via so as to relieve stress when assembling or better route connections.

The glass of the hermetic feedthrough is coated on both sides with biocompatible insulative layer 436 of silicon carbide (SiC) or $Al_2O_3$+$HfO_2$/$ZrO_2$. The vias are not coated, except that the insulative layer overlaps a bit on the edges of the vias, enough to cover the interface where the doped silicon via and glass meet. An underfill may be applied between the lower ASIC 421 and hermetic feedthrough 424.

An insulative layer is optional. In some embodiments, the insulative coating is only on the thin film (ribbon cable underneath) side, and on others Polymer (polyimide) ribbon cable 404 connects its conductors 454 to underside metal caps 434. The conductors then run through the cable to a distal end in which electrodes are fashioned. The electrodes can connect with tissue to read electrical signals or stimulate the tissue. For example, the electrodes may be inserted into the brain, eye, or other organs of a subject. The conductors may be individually coated with silicon carbide within the polymer of the ribbon cable.

Walls surrounding the chips may be fused, such as by laser welding, adhesive, or other metal-to-metal bonding, in place. In the figure the walls are stacked three high, but other numbers of walls may be stacked or integrated in place.

Figure 5:
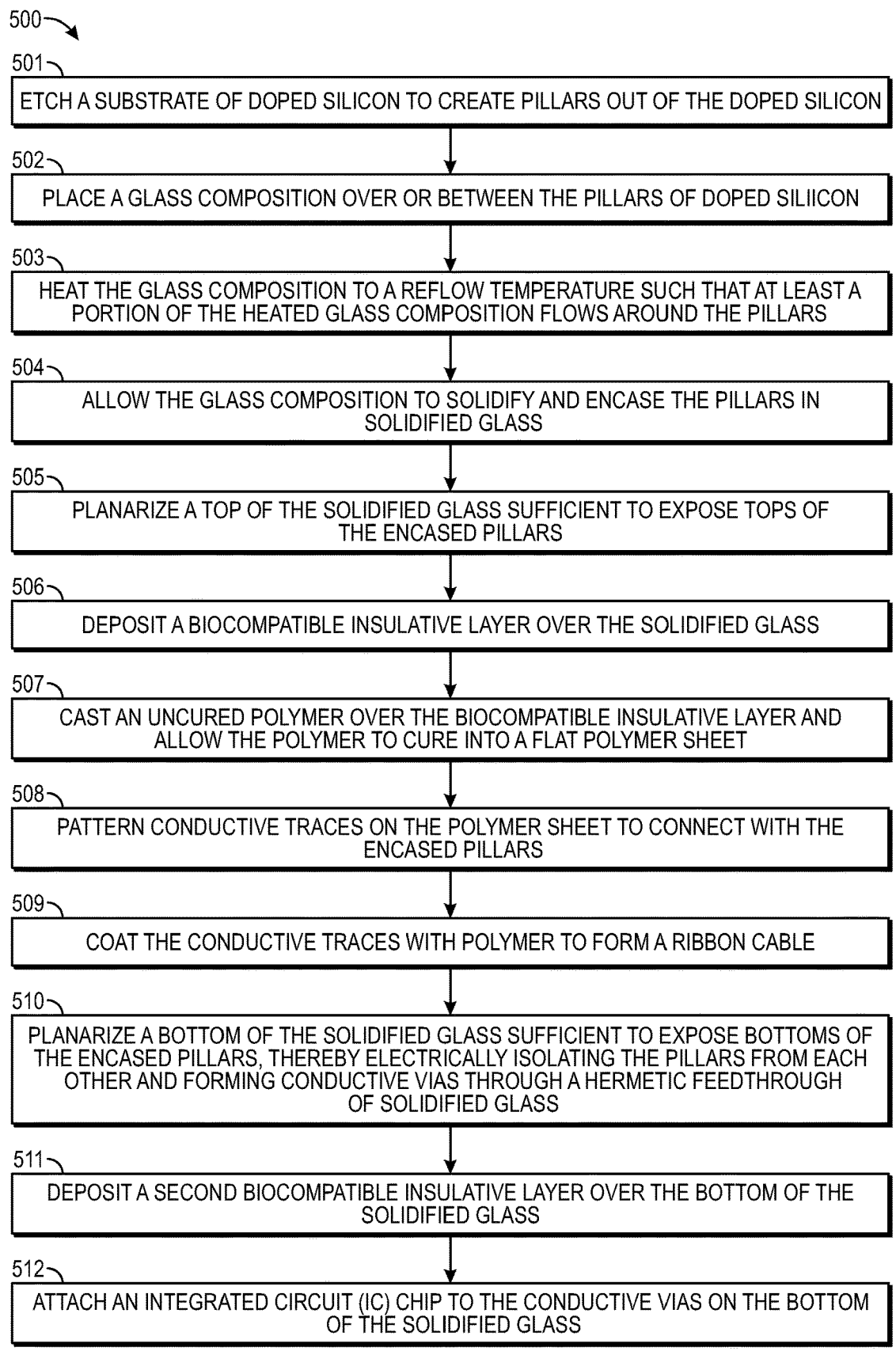
FIG. 5 is a flowchart illustrating an embodiment in accordance with the present invention.

FIG. 5 is a flowchart of a process 500 in accordance with an embodiment. In operation 501, a substrate of doped silicon is etched to create pillars out of doped silicon. In operation 502, a glass composition is placed over the pillars of doped silicon. In operation 503, the glass composition is heated to a reflow temperature such that at least a portion of the heated glass composition flows around the pillars. In operation 504, the glass composition is allowed to solidify and encase the pillars in solidified glass. In operation 505, a top of the solidified glass is planarized sufficient to expose tops of the encased pillars. In operation 506, a biocompatible insulative layer is deposited over the solidified glass. In operation 507, an uncured polymer is cast over the biocompatible insulative layer and allowed to cure into a flat polymer sheet. In operation 508, conductive traces are patterned on the polymer sheet to connect with the encased pillars. In operation 509, the conductive traces are coated with polymer to form a ribbon cable. In operation 510, a bottom of the solidified glass and silicon is planarized to expose bottoms of the encased pillars. This electrically isolates the pillars from each other and forms conductive vias through a hermetic feedthrough of solidified glass. In operation 511, a second biocompatible insulative layer is deposited over the bottom of the solidified glass. In operation 512, an integrated circuit chip is attached to the conductive vias on the bottom of the solidified glass.

FIGS. 6A-6K illustrate steps in a manufacturing process of a glass hermetic feedthrough and integrated flex/ribbon cable.

Figure 6A:
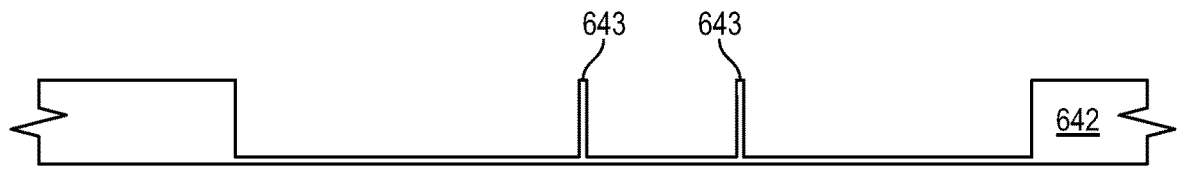
FIG. 6A illustrates etching pillars of doped silicon in a substrate in a manufacturing process in accordance with an embodiment.

FIG. 6A illustrates etching pillars in substrate of doped silicon 642. Viewed in the figure is a small portion of the much wider six-inch (152 mm) diameter silicon wafer. At about 300 μm tall, pillars 643 of doped silicon are small in comparison to the width of the wafer. The boron-doped-silicon pillars are electrically conductive, to an extent, and will ultimately serve as the conductive vias for the hermetic feedthrough.

In alternative embodiments, the silicon pillars can be replaced by metal pillars. This includes etching away the silicon pillars and then using electroplating or other additive steps using metal pastes and powders that are sintered or thermocompressed to fill in where the silicon pillars were.

In yet another embodiment, pillars can be made of metal first (metal plated through a sacrificial mold or array of wires). Preferably, they should be of a metal that matches the coefficient of thermal expansion for glass, like molybdenum, tungsten, or tantalum, in order to have a sealed metal-glass interface after the glass reflow step. A thin metal oxide should also be grown on the metal prior to glass reflow for better wetting and adhesion between the pillar and glass.

Figure 6B:
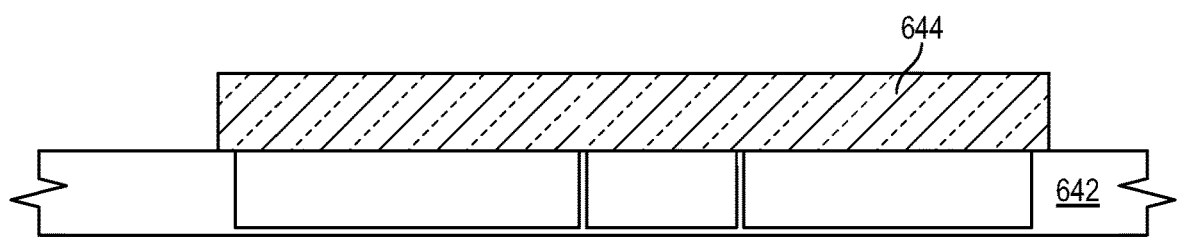
FIG. 6B illustrates placing a glass composition over the pillars in a manufacturing process in accordance with an embodiment.

FIG. 6B illustrates a tiny slide of glass composition 644 being placed over the pillars. The glass composition may be several hundred microns thick, having enough bulk material to fill the recessed basins between the pillars/columns.

Figure 6C:
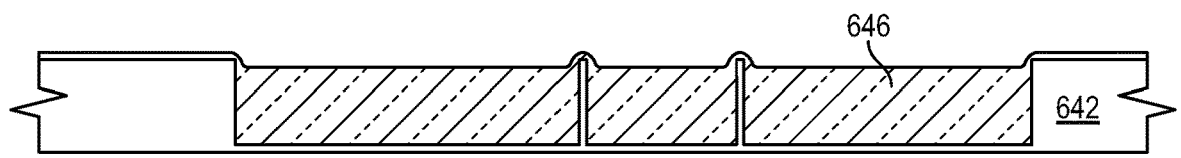
FIG. 6C illustrates heating the glass composition to reflow in a manufacturing process in accordance with an embodiment.

FIG. 6C illustrates reflowing the glass composition in the presence of high temperatures. The glass composition slumps into the recesses and flows into the corners near the pillars, surrounding them with glass 646. The pillars, made of silicon, have a higher melt temperature and thus do not melt or slump. Because the glass reflows as a liquid under pressure to minimize its potential energy, it fills all spaces and seals tightly at the molecular level against the pillars. There are virtually no gaps. This hermetic sealing can be assured at large scales, including thousands of pillars.

Empty voids in the silicon mold can reduce trapped gas from preventing glass filling the mold, and the pressure difference pushes glass into the corners. Increasing the surface wettability of the silicon can help the glass spread against all corners. This can be accomplished by roughening, plasma surface treatments, or applying a layer of wetting material on the surfaces between the pillars.

As the glass cools, it hardens and encases the pillars. The result is electrically conductive columns/pillars encased in insulative glass. The top of the glass is dominated by a wavy, hardened meniscus that is not perfectly flat or otherwise suitable for bonding electronic components. This is an artifact of surface tension between the glass and silicon after glass flows into the silicon mold.

Figure 6D:
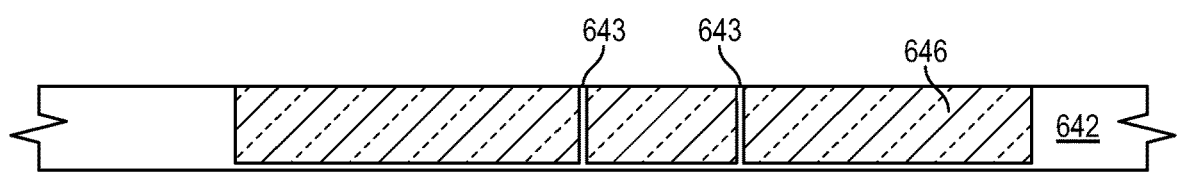
FIG. 6D illustrates planarizing a top of the now solidified glass composition in a manufacturing process in accordance with an embodiment.

FIG. 6D illustrates grinding and polishing the top of the solidified glass to form a flat top surface. The wavy undulations of the previous figure give way to an ultra-flat surface that is suitable for microfabrication of precise further layers. Grinding is just one way of planarizing the silicon-glass composition.

"Planarizing" includes making into a flat plane, such as by grinding flat, chemical or mechanical polishing, laser ablation, or as otherwise known in the art.

Figure 6E:
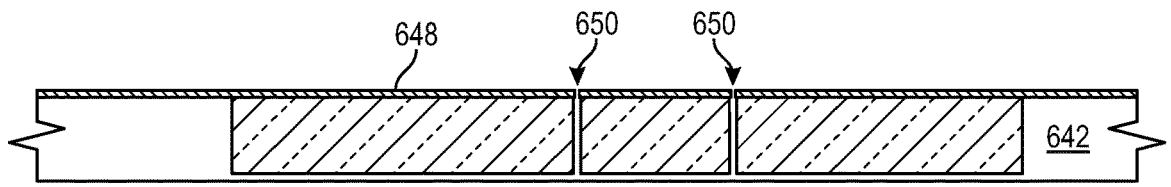
FIG. 6E illustrates the chemical vapor deposition (CVD) of a biocompatible insulative layer in a manufacturing process in accordance with an embodiment.

FIG. 6E illustrates the plasma-enhanced chemical vapor deposition (PECVD) of silicon carbide (SiC) over the ground and flattened surface to form insulative layer 648. The layer of silicon carbide overlaps a little over the perimeter of the top of each via, leaving a center portion of the top of the via exposed as gaps 650. The silicon carbide is an electrically insulative layer that helps protect the glass from body fluids in case microcracks occur.

Figure 6F:
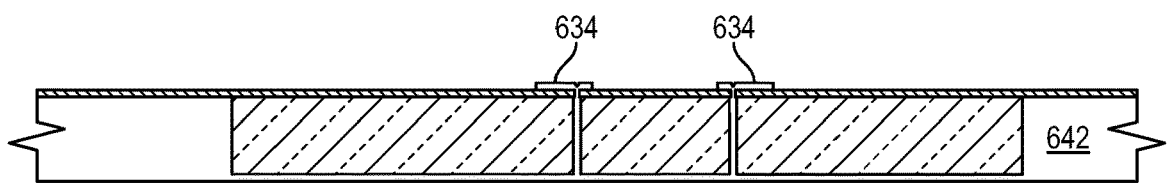
FIG. 6F illustrates depositing metal caps in a manufacturing process in accordance with an embodiment.

FIG. 6F illustrates depositing a metal layer that could include titanium, platinum, gold, or other metals to form metal caps 634 over the vias, partially filling in the recesses formed by the silicon carbide. It is a conformal deposition process. Metal caps 634 extend over the silicon carbide. The caps are elongated, extending over the silicon carbide to one side more than another side. Each metal cap 634 forms a pad onto which a connection may be made. A rectangular array of metal cap pads provides suitable connections for a ball grid array (BGA) IC chip to be affixed.

An additional layer of silicon carbide can be optionally deposited on top of the layer of silicon carbide and alongside the metal caps in order to protect the silicon and silicon-glass interface from body fluids.

Figure 6G:
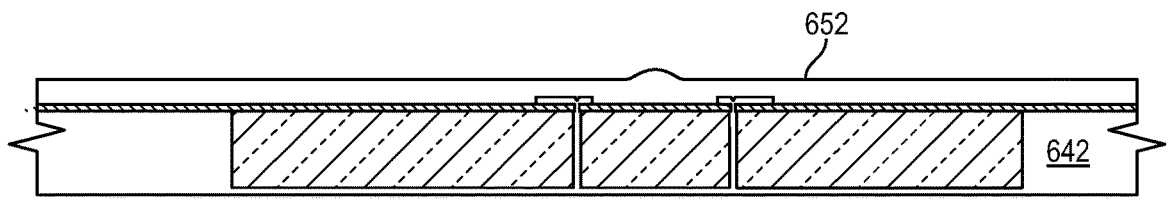
FIG. 6G illustrates casting an uncured polymer in a manufacturing process in accordance with an embodiment.

FIG. 6G illustrates casting an uncured polymer by spinning liquid, uncured polyimide over the glass panel. The polymer is the first layer of a monolithically laid up flexible ribbon cable. The remains of a dollop of liquid polymer is shown centered above the two pillars but can be almost anywhere near the center of the wafer. The polyimide is allowed to at least partially cure after it has flattened out into flat polymer sheet 652.

"Casting" an uncured polymer includes drop-casting, spray-coating, spin-coating, molding, printing, or any combination of these techniques including curing, or as otherwise known in the art. It may be followed by planarization and/or etching back if needed to achieve final dimensions.

Figure 6H:
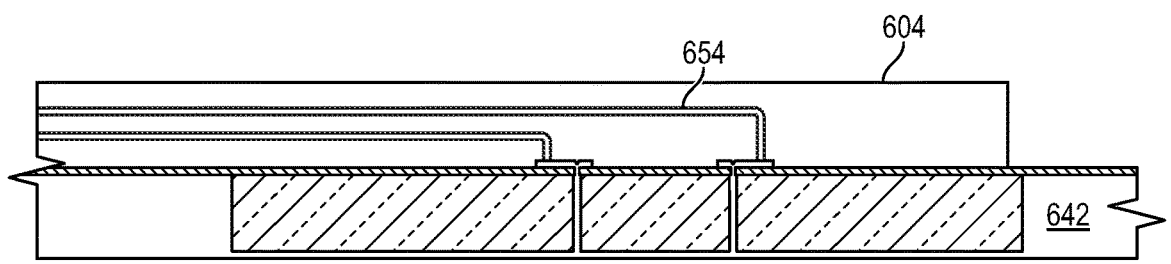
FIG. 6H illustrates patterning conductive traces and coating them with polymer to form a thin film ribbon cable in a manufacturing process in accordance with an embodiment.

FIG. 6H illustrates the result of photolithographically defining conductive traces 654 and encasing them with more polyimide to form the rest of the ribbon cable 604, complete with its own vias and metal traces. The build up of other layers of polyimide may be aided by not letting the first layer fully cure until other layers of polyimide are laid atop. That will promote cross-linking between any uncured polymer in the first layer and the second layer.

The polyimide of the cast layer has been cut or patterned so that it is a thin ribbon strip off to one side.

Figure 6I:
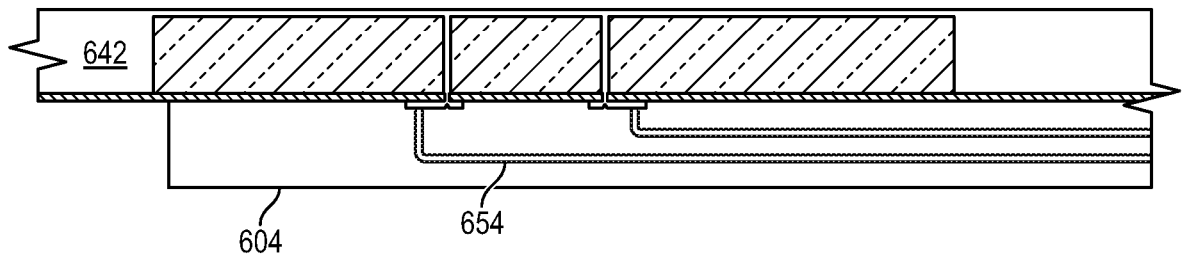
FIG. 6I illustrates flipping the workpiece over in a manufacturing process in accordance with an embodiment.

FIG. 6I illustrates the same feedthrough and ribbon cable as in FIG. 7H but flipped upside-down (with respect to the Earth's gravitation) for further processing.

Figure 6J:
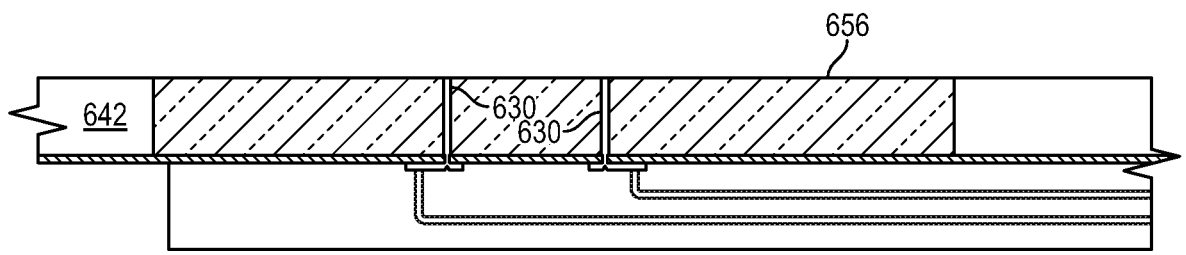
FIG. 6J illustrates planarizing a bottom of the solidified glass in a manufacturing process in accordance with an embodiment.

FIG. 6J illustrates grinding silicon from what was once the bottom of the silicon substrate wafer to form smooth surface 656. This electrically isolates the conductive boron-doped silicon vias 630 from one another. It is now readily apparent that the reflowed and ground glass is in the form of a glass slide interspersed with conductive vias 630. This is a hermetic feedthrough: hermetic because it is tightly sealed, and a feedthrough because it has electrical connections from one side to the other.

One may replacing the pillars of silicon with pillars of metal by etching away the silicon pillars and electroplating or additively filling metal in their place.

Figure 6K:
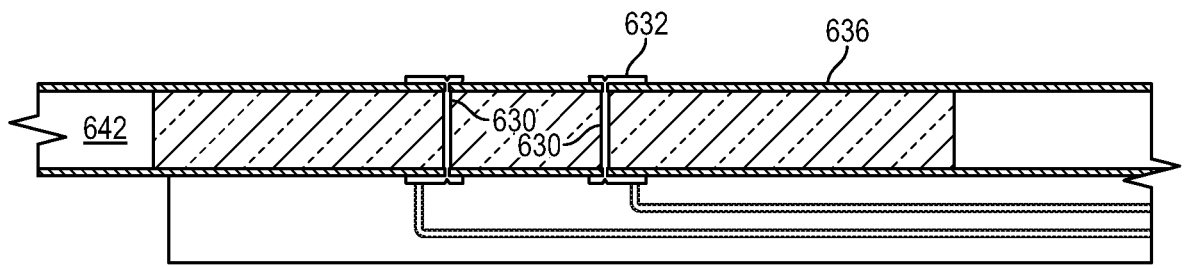
FIG. 6K illustrates depositing a second biocompatible insulative layer and metal caps over the bottom in a manufacturing process in accordance with an embodiment.

FIG. 6K illustrates depositing a layer of silicon carbide 636 on the glass slide, overlaying the perimeters of conductive vias 630. It also shows metal caps 632 deposited on the vias with extensions over the silicon carbide. An optional second layer of silicon carbide may be next in the process but is not shown.

A more complete listing of manufacturing steps, in order of operation, is included below. The particular order of steps, or subsections, shown here may be altered. For example, forming the thin film side and the chip side may be done in different orders.

Substrate Fabrication
   Photolithography
   Si deep reactive-ion etching (DRIE)
   Mask strip
   Increase surface wettability of silicon
   Wafer bonding
   Reflow glass
Planarize glass & silicon side 1
Thin Film/Ribbon Cable Fabrication
   Planarize glass & silicon (if side 2)
   Photolithography
   Metal deposition & selective removal
   Deposit silicon carbide (SiC) insulative layer
   Photolithography
   Etch SiC
   Resist strip
   Cast & cure polyimide
   Deposit SiC
   Photolithography
   Metal deposition & selective removal
   Deposit SiC
   Photolithography
   Etch SiC
   Resist strip
   Cast & cure polyimide
   Photolithography
   Etch polyimide
   Resist strip
   Photolithography
   Electrode metal deposition & selective removal
'Chip Side' Fabrication
   Planarize glass & silicon (if side 2)Photolithography
   Metal deposition & selective removal
Optional on chip side
   Deposit insulative layer such as SiC
   Photolithography
   Etch insulative layer
Device Singulation and Release
   Photolithography
   Etch silicon
   Release After the hermetic feedthrough and ribbon cable are fabricated, the electronics can be attached. An IC chip, such as lower ASIC 421 (see FIG. 4), can be joined to a ball grid array formed by the metal caps. An epoxy underfill (or dry underfill) can be injected between the IC chip and hermetic feedthrough for mechanical support of the bonds. Walls or an enclosure can be fused, such as by welding, laser welding, metal-metal bonding, brazing, or solder bonding. Another glass hermetic feedthrough can be fused on top to form a hermetically sealed box.

It should be appreciated that a brain implant or other system and a respective control system for the brain implant can have one or more microprocessors/processing devices that can further be a component of the overall apparatuses. The control systems are generally proximate to their respective devices, in electronic communication (wired or wireless) and can also include a display interface and/or operational controls configured to be handled by a user to monitor the respective systems, to change configurations of the respective systems, and to operate, directly guide, or set programmed instructions for the respective systems, and sub-portions thereof. Such processing devices can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

In some embodiments, the systems and methods of the present disclosure can be used in connection with neurosurgical techniques. However, one skilled in the art would recognize that neurosurgical techniques are a non-limiting application, and the systems and methods of the present disclosure can be used in connection with any biological tissue. Biological tissue can include, but is not limited to, the brain, muscle, liver, pancreas, spleen, kidney, bladder, intestine, heart, stomach, skin, colon, and the like.

The systems and methods of the present disclosure can be used on any suitable multicellular organism including, but not limited to, invertebrates, vertebrates, fish, birds, mammals, rodents (e.g., mice, rats), ungulates, cows, sheep, pigs, horses, non-human primates, and humans. Moreover, biological tissue can be ex vivo (e.g., tissue explant), or in vivo (e.g., the method is a surgical procedure performed on a patient).

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. A method of manufacturing a biocompatible hermetic feedthrough with integrated ribbon cable, the method comprising:
    placing a glass composition over or between pillars of doped silicon;
    heating the glass composition to a reflow temperature such that at least a portion of the heated glass composition flows around the pillars;
    allowing the glass composition to solidify and encase the pillars in solidified glass;
    planarizing a top of the solidified glass sufficient to expose tops of the encased pillars;
    depositing a biocompatible insulative layer over the solidified glass;
    casting an uncured polymer over the biocompatible insulative layer and allowing the polymer to cure into a flat polymer sheet;
    patterning conductive traces on the polymer sheet to connect with the encased pillars;
    coating the conductive traces with polymer to form a ribbon cable; and
    planarizing a bottom of the solidified glass sufficient to expose bottoms of the encased pillars, thereby electrically isolating the pillars from each other and forming conductive vias through a hermetic feedthrough of solidified glass.

2. The method of claim 1 wherein the biocompatible insulative layer covering the solidified glass composition comprises silicon carbide or $Al_2O_3$+$HfO_2$/$ZrO_2$.

3. The method of claim 1 further comprising:
    etching a substrate of doped silicon to create the pillars out of doped silicon.

4. The method of claim 1 further comprising:
    replacing the pillars of silicon with pillars of metal by etching away the silicon pillars and electroplating or additively filling metal in their place.

5. The method of claim 1 further comprising:
    depositing metal caps over the tops of the encased pillars, wherein the conductive traces connect with the conductive vias through the metal caps.

6. The method of claim 5 wherein at least one of the metal caps on the bottom of the solidified glass is elongated and overhangs away from a respective via.

7. The method of claim 1 further comprising:
    depositing a second biocompatible insulative layer over the bottom of the solidified glass; and
    attaching an integrated circuit (IC) chip to the conductive vias on the bottom of the solidified glass.

8. The method of claim 7 wherein the attaching includes compressing a bump connection between the IC chip and at least one of the conductive vias.

9. The method of claim 7 wherein the attaching includes soldering, using anisotropic conductive film (ACF) connections, or applying epoxy.

10. The method of claim 7 further comprising:
    attaching a hermetically sealed walled housing around the IC chip and encasing the IC chip.

11. The method of claim 10 wherein encasing the IC chip comprises:
    attaching a second hermetic interconnect to walls around the IC chip.

12. The method of claim 1 wherein planarizing includes grinding, polishing, lapping, fly cutting, laser ablating, or coating with a planarizing layer and etching.

13. The method of claim 1 wherein the planarizing of the bottom of the solidified glass occurs before casting the uncured polymer.

14. A monolithic, biocompatible feedthrough apparatus comprising:
    a glass substrate having doped silicon conductive vias produced by reflowing a molten glass composition around etched pillars of doped silicon and allowing the glass composition to solidify and encase the etched pillars in solidified glass;
    a biocompatible insulative layer covering a surface of the glass substrate;
    a polymer ribbon cable formed from uncured polymer curing on the biocompatible insulative layer; and
    conductive traces within the polymer ribbon cable and connecting with the conductive vias.

15. The apparatus of claim 14 wherein the biocompatible insulative layer covering the surface of the glass substrate comprises silicon carbide or $Al_2O_3$+$HfO_2$/$ZrO_2$.

16. The apparatus of claim 14 further comprising:
    biocompatible metal caps covering ends of the conductive vias,
    wherein the conductive traces connect with the conductive vias through the biocompatible metal caps.

17. The apparatus of claim 16 wherein at least one of the biocompatible metal caps is elongated and overhangs away from a respective via.

18. The apparatus of claim 14 further comprising:
    a second biocompatible insulative layer over a bottom of the glass substrate; and
    an integrated circuit (IC) chip attached to the conductive vias on the bottom of the glass substrate.

19. The apparatus of claim 18 wherein the IC is attached by compressing a bump connection between the IC chip and at least one of the conductive vias.

20. The apparatus of claim 18 further comprising:
    a hermetically sealed walled housing around the IC chip and encasing the IC chip.

21. The apparatus of claim 14 wherein a surface of the etched pillars has been treated to increase wettability.

22. The apparatus of claim 21 wherein the surface of the etched pillars has been roughened, treated with plasma, or coated with wetting material in order to increase wettability.

23. The apparatus of claim 21 further comprising:
a layer of metal oxide between the etched pillars and the solidified glass.

\* \* \* \* \*